(12) United States Patent
Jaworski et al.

(10) Patent No.: US 6,478,440 B1
(45) Date of Patent: Nov. 12, 2002

(54) NIGHT LIGHT AIR FRESHENER

(75) Inventors: Thomas Jaworski, Racine, WI (US);
Tadahiko Nakagaki, Singapore (SG);
Michael Thomas Milo, Singapore
(SG); Kong Wai Ki, Singapore (SG);
Patrick Yeo Siok Hui, Singapore (SG)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/523,006

(22) Filed: Mar. 10, 2000

(51) Int. Cl.[7] .............................................. F21V 33/00
(52) U.S. Cl. ........................ 362/96; 362/95; 362/226; 362/253; 362/290; 362/802
(58) Field of Search .............................. 362/92, 95, 96, 362/226, 253, 290, 802, 276; 428/905; 439/929

(56) References Cited

U.S. PATENT DOCUMENTS

| | | |
|---|---|---|
| 2,942,090 A | 6/1960 | Diehl |
| 3,780,260 A | 12/1973 | Elsner |
| 4,084,079 A | 4/1978 | Costello |
| 4,277,542 A * | 7/1981 | Boonstra et al. ............ 338/308 |
| 4,549,250 A | 10/1985 | Spector |
| 4,837,421 A | 6/1989 | Luthy |
| 4,849,606 A | 7/1989 | Martens et al. |
| 5,481,442 A * | 1/1996 | Dickie et al. ................. 362/95 |
| 5,556,192 A | 9/1996 | Wang |
| 5,937,140 A | 8/1999 | Leonard et al. |

* cited by examiner

Primary Examiner—Sandra O'Shea
Assistant Examiner—Guiyoung Lee

(57) ABSTRACT

An air freshener dispenser is taught having plug-through capability as well as a night light. The dispenser is a plug-in diffuser for such active materials as fragrances and air fresheners, and eliminates the consumer problem of loss of an electrical outlet, by providing a receptacle into which another plug may be inserted. The dispenser uses replaceable cartridges of material to be dispensed, and provides a night light for those who desire such.

14 Claims, 5 Drawing Sheets

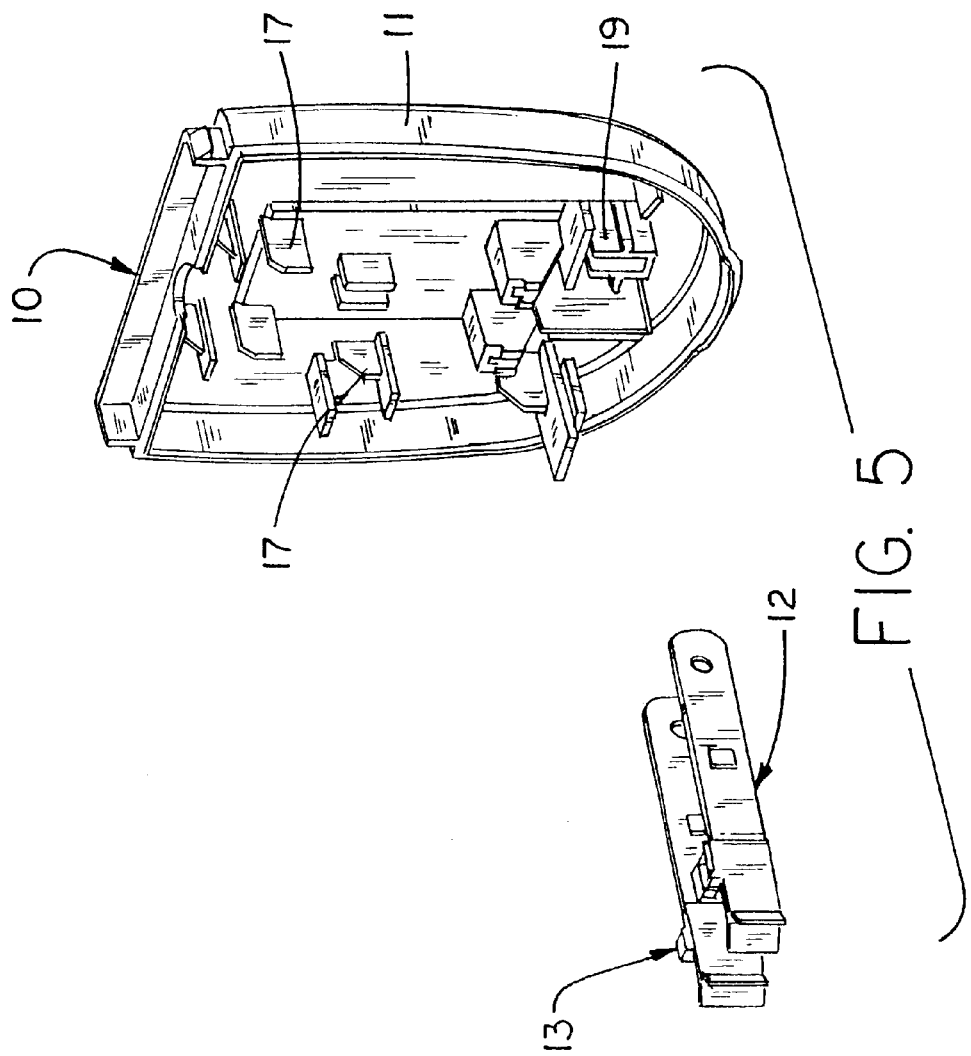

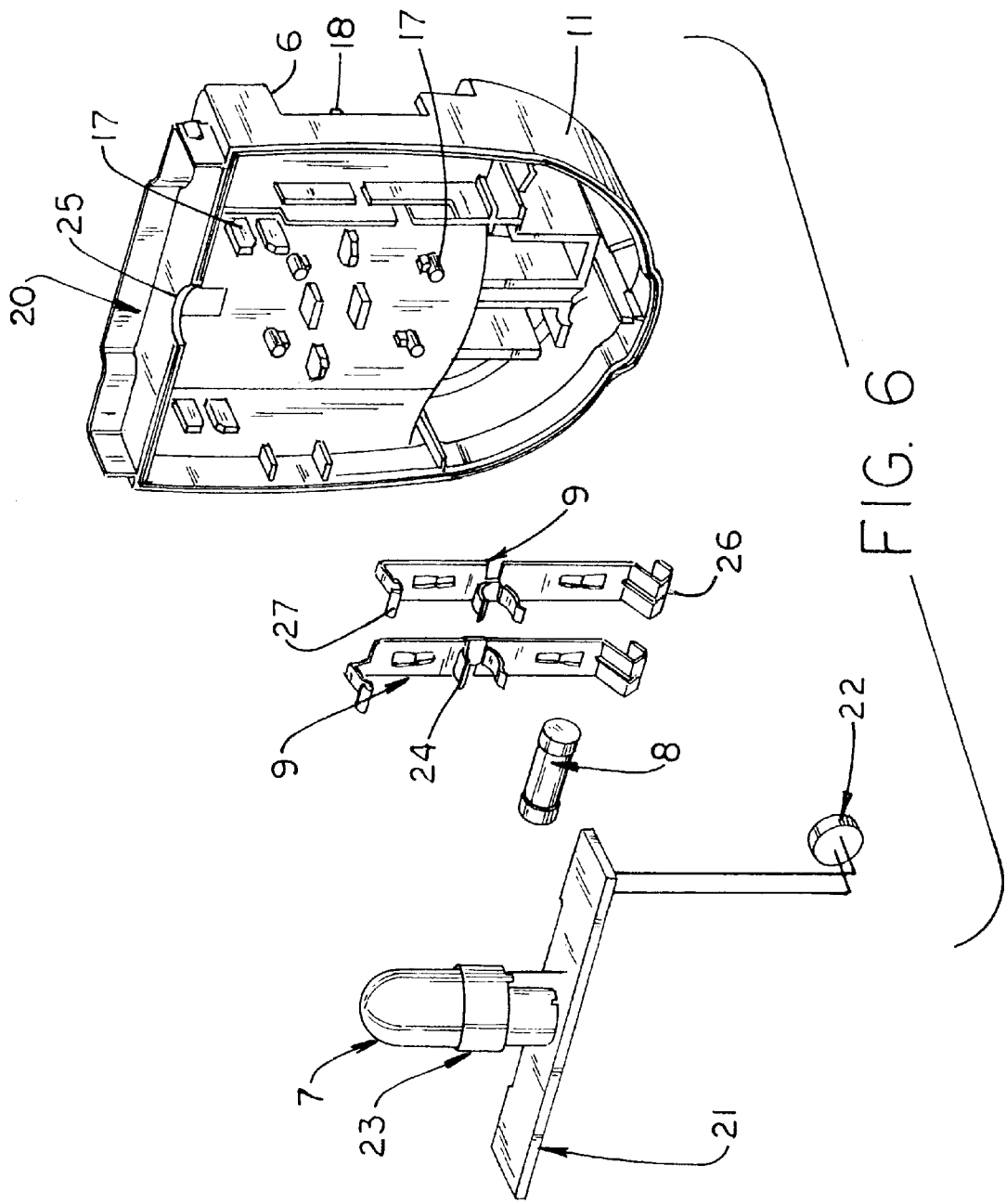

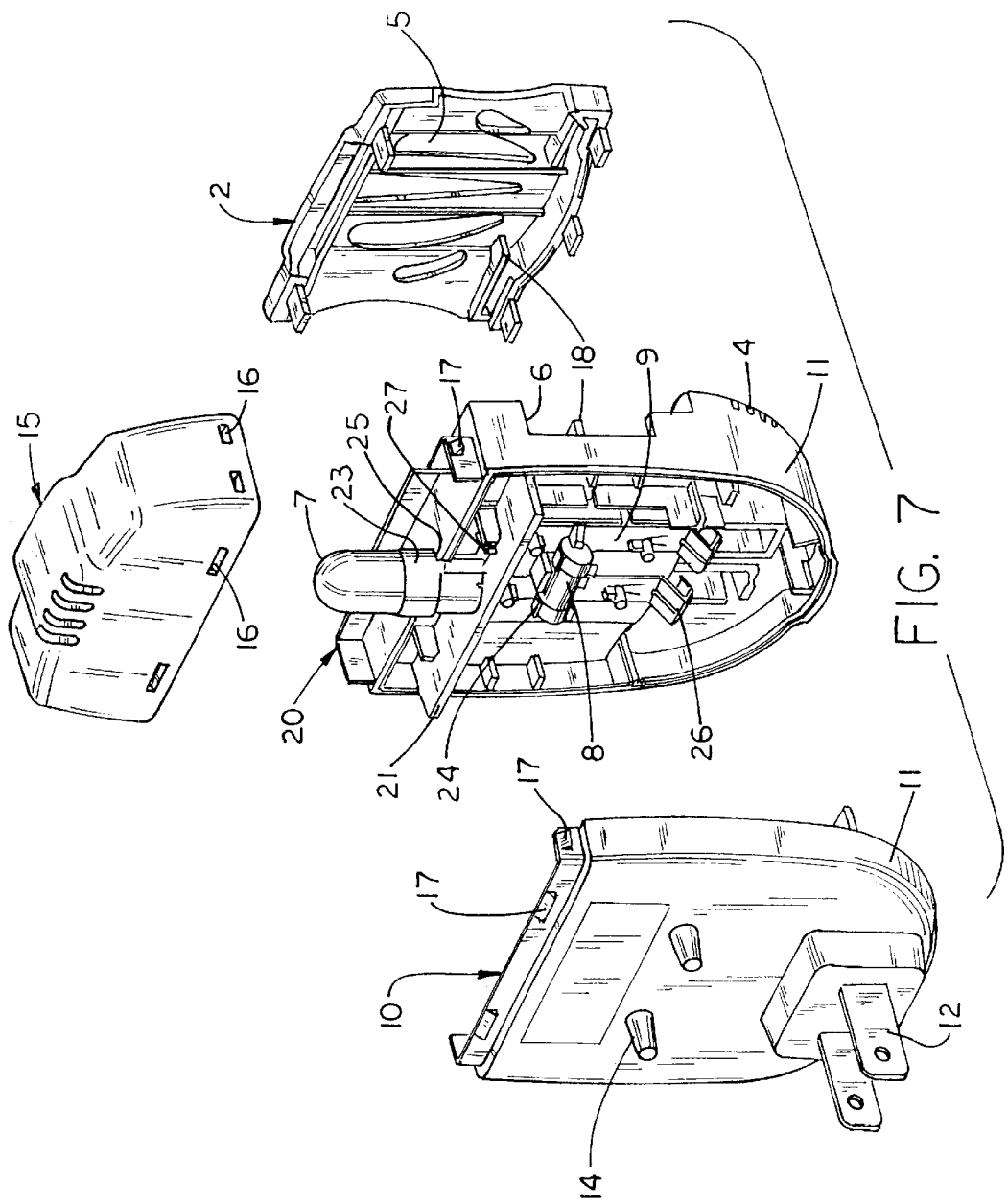

NIGHT LIGHT AIR FRESHENER

RELATED APPLICATION(S)

Not applicable.

FEDERALLY SPONSORED RESEARCH OR DEVELOPMENT

Not applicable.

BACKGROUND OF INVENTION

1. Technical Field

The present invention relates generally to dispensers of vaporizable materials. More specifically, the invention relates to an improvement in devices for dispensing a fragrance or air freshener, or other material, in the form of a vapor for air freshening, insect control, or other purpose, in an enclosed environment. The improvement disclosed herein relates broadly to an electrical plug-in air freshener device or insect control system, of the type frequently referred to as a fragrance warmer or plug-in diffuser, specifically wherein the device further provides both a plug-through outlet and a small electric lamp.

2. Background Art

The need for effectively combating airborne malodors in homes and enclosed public buildings, by odor masking or destruction, is well established, as is the dispensing of insect control materials for killing or deterring insects. Various kinds of vapor-dispensing devices have been employed for these purposes. The most common of such devices is the aerosol container which propels minute droplets of an air freshener composition into the air. Another common type of dispensing device is a dish containing or supporting a body of gelatinous matter which, when it dries and shrinks, releases a vaporized composition into the atmosphere. Other products, such as deodorant blocks, are also used for dispensing air-treating vapors into the atmosphere by evaporation. Another group of vapor-dispensing devices utilizes a carrier material such as paperboard or a porous plastic or ceramic, impregnated or coated with a vaporizable composition.

A number of recent developments include a liquid or gel air-treating composition in an enclosure, all or part of which is formed of a polymeric film through which the air-treating composition can migrate to be released as a vapor at an outer surface. The use of this type of permeable polymeric membrane controls the dispensing of air-treating vapors, and tends to eliminate great variations in rate of dispensing over the life of the product.

Wicking devices are also well known for dispensing volatile liquids into the atmosphere, such as fragrance, deodorant, disinfectant, or insecticide active agent. A typical wicking device utilizes a combination of a wick and an emanating region to dispense a volatile liquid from a liquid reservoir. Typical wicking devices are described in U.S. Pat. Nos. 1,994,932; 2,597,195; 2,802,695; 2,804,291; 3,550,853; 4,286,754; 4,413,779; 4,454,987; 4,913,350; and 5,000,383; all of which are incorporated herein by reference.

Of special interest with respect to the present invention are wicking dispenser devices in which the wicking action is promoted by a heat source. This type of wicking device is described in U.S. Pat. Nos. 3,288,556; 3,431,393; 3,482,929; 3,633,881; 4,020,321; 4,968,487; 5,038,394; 5,290,546; and 5,364,027; all of which are incorporated herein by reference.

Additional dispensers of the type often referred to as plug-in diffusers described in U.S. Pat. Nos. 4,849,606, and 5,937,140, which are assigned to S. C. Johnson & Son, Inc., of Racine, Wis., both of which are incorporated herein by reference. Of these references, it is noted that U.S. Pat. No. 5,937,140 discloses a fragrance warmer incorporating plug-though capability. The present invention constitutes an improvement upon this reference, adding an integral night light feature and novel electrical circuitry in a unit providing for simpler, less expensive assembly.

In addition to the above, Luthy discloses, in U.S. Pat. No. 4,837,421, a fragrance dispenser which releases a fragrance from a solid polyamide resin body. The dispenser includes a housing, having at least one opening, disposed adjacent to the resin. A heating resistor is provided in the housing for maintaining an elevated temperature, and a thermally conductive metal heating plate is arranged in the housing in thermally conductive relationship with the heating resistor and configured to at least partially surround and contact the resin body containing the fragrance.

Wang, in U.S. Pat. No. 5,556,192, discloses a perfumer with an optically controlled night lamp. The perfumer includes a heat conductor wrapped by a heat conductive and fireproof plastic material for generating heat to vaporize a solid perfume, and uniformly disperse the perfume gas. The night lamp is disposed within the perfumer structure and is controlled by an optically sensitive element which turns the lamp on or off in accordance with ambient illumination. The perfumer is powered by a power plug consisting of a pair of identical copper plates having a heat conductor welded there between to form a circuit.

Spector teaches, in U.S. Pat. No. 4,549,250, a night lamp assembly wherein a low wattage bulb illuminates removable transparent slides placed at the front of the assembly. The rear face of the slide is coated or impregnated with a volatile coating to produce a fragrance as the slide is heated by the lamp.

In addition, the incorporation of night lights into electrical vaporizers is also taught in U.S. Pat. No. 2,942,090, of Diehl, U.S. Pat. No. 3,780,260, of Elsner, and U.S. Pat. No. 4,084,079, of Costello. These references, however, fail to provide the convenience and economy of the present invention.

As indicated, it is well known to provide electrical heating devices for dispensing such materials as air fresheners, deodorizers, and insect control materials. Such devices often comprise a liquid reservoir of liquid to be dispensed, an electric heater to warm the liquid to cause it to vaporize more readily, and an electrical plug to plug the device into an electric outlet for power. However, it is also known that if such devices are plugged into the lower of two vertically oriented outlets, the consumer may choose to employ the upper outlet for another plug-in apparatus, such as a night light, or an electrical cord for an appliance. Such apparatus may be subject to damage or deterioration from the vapors or fumes of the liquid material which is heated and dispensed, possibly resulting in the exposure of live electrical parts, since it is known that many of the fragrance oils used in the preparation of such dispensers contain solvents which dissolve or react with such plastics as styrene, which is frequently used for night light assemblies due to its low cost and formability. Moreover, the use of such prior art dispensers results in the loss or sacrifice of an electrical outlet, frequently in an area where extra outlets are at a premium, such as on a kitchen or bathroom counter. This is particularly a problem when such dispensers are of such a dimension as to completely cover a vertically oriented wall receptacle, thus utilizing one of the two outlets therein, and covering the second.

SUMMARY OF INVENTION

The present invention overcomes these deficiencies of the prior art, by incorporating both a night light and a plug through outlet directly into the structure of the plug-in diffuser or fragrance warmer, said diffuser being of a size that when it is plugged into the upper outlet of a vertically oriented wall receptacle, it does not preclude use of the lower outlet. Thus, the consumer need not lose the use of an electrical outlet to plug in the present diffuser, since this unit provides for a plug through connection to the wall outlet. Further, the consumer simultaneously gains a night light, since the present invention incorporates a low cost lamp directly into the dispensable assembly of the unit. Thus, the consumer obtains both an air freshener or diffuser and a night light, at a relatively low cost, while not losing the use of an electrical outlet, since the invention provides a plug through feature, permitting use of both outlets of a dual outlet receptacle for plugging in appliances, table lamps, etc.

In one aspect, the invention provides a combination night light and electrical vaporizer, with the added advantage of a plug through feature by which an additional plug may be inserted. The night light feature of the invention comprises a built-in low wattage bulb, with optional circuitry to be automatically turned off or on in response to ambient illumination. The electrical vaporizer comprises a plug-in diffuser in conjunction with a substance to be thermally diffused, said substance being retained in a container subject to being heated by an electrical resistance heater. A further feature of the invention is the presence of connector sockets into which an external plug may be inserted, with connector prongs present for insertion into a wall outlet or socket. This connector thus provides an electrical bridge by which an external device may be electrically connected to the wall outlet circuitry. Such connectors may comprise first and second electrical assemblies, including a male terminal and a female terminal electrically connected to the male terminal, with a heater element situated between dual heat transfer plates positioned so as to provide heat to the container of the substance to be thermally diffused.

In one form, the invention comprises a low cost, disposable, refillable air freshener device, having a suggested life span predetermined by the life span of a non-replaceable night light bulb. In this manner, the consumer may replace the air freshener container, such as when the contents thereof have been fully utilized, to change the function of the device, or for aesthetic reasons, such as a desire for a specific fragrance. In this embodiment, the consumer may replace an air freshener element or container with an insecticide element or container, if desired, or with any active suitable for diffusion or evaporation from a container subject to heating to evaporate or diffuse such active material. Active materials which are suitable for inclusion in the container placed in the receiving chamber of the plug-in diffuser of the present invention include volatile active materials selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof. Moreover, it is possible for the consumer to continue use of the diffusion device, absent the night light feature after the night light bulb has expended its full life span, without loss of the plug-through feature of the dispenser, if he so chooses.

In the preferred embodiment of the invention, a thermal diffuser of an active material is provided, comprising a housing of a suitable material, such as polypropylene, an electric resistance heater, such as a metal oxide resistor, a night light, and plug-through electrical circuitry.

Thus, the present invention comprises a plug-in diffuser, for use with a substance to be thermally diffused, said diffuser comprising an outer housing, a male electrical plug extending outwardly from the rear of said housing, a female electrical receptacle on the front of said housing having direct electrical contact with said male electrical plug providing plug-through capability, an opening in said outer housing for receipt of an active material container, said opening being located between the front cover of said housing and an inner wall within said housing, an electrical resistance heater electrically connected between the terminals of said male electrical plug by means of parallel electrically conductive metal heat transfer plates extending from said male electrical plug terminals to a night light circuitry board electrically connected between said parallel metal plates within said housing, said metal heat transfer plates being in heat transfer contact with said inner wall of said housing, and an electric night light electrically connected to said night light circuitry board, and having a night light lens over said night light and affixed to said housing.

The present invention further comprises a plug-in diffuser wherein said housing is a moldable plastic, said active material container comprises a tray receptacle having a vapor permeable plastic cover, said active material is selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof, said night light circuitry contains an on/off switch, or optionally an automatic on/off circuit with a sensor control, and the night light bulb is not replaceable.

Still further, the present invention comprises an electrically heated dispenser of active materials, said dispenser having a night light and plug-through electrical circuitry, wherein the container of said active materials comprises a plastic tray having a vapor permeable cover over an active material selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof, said heater comprises a metal oxide resistor, and the circuitry for said night light comprises an automatic control for said night light.

These and still other embodiments and advantages of the present invention will be apparent from the description which follows. The following description is merely of the preferred embodiments. Thus, the claims should be looked to in order to understand the full scope of the invention.

BRIEF DESCRIPTION OF DRAWINGS

FIG. 5 is an exploded cutaway illustration of the plug deck assembly of said diffuser.

FIG. 6 is an exploded cutaway illustration of main housing of said diffuser.

FIG. 7 is an exploded cutaway illustration of the entire assembly of said diffuser.

DETAILED DESCRIPTION OF THE INVENTION

Figures 1, 2:
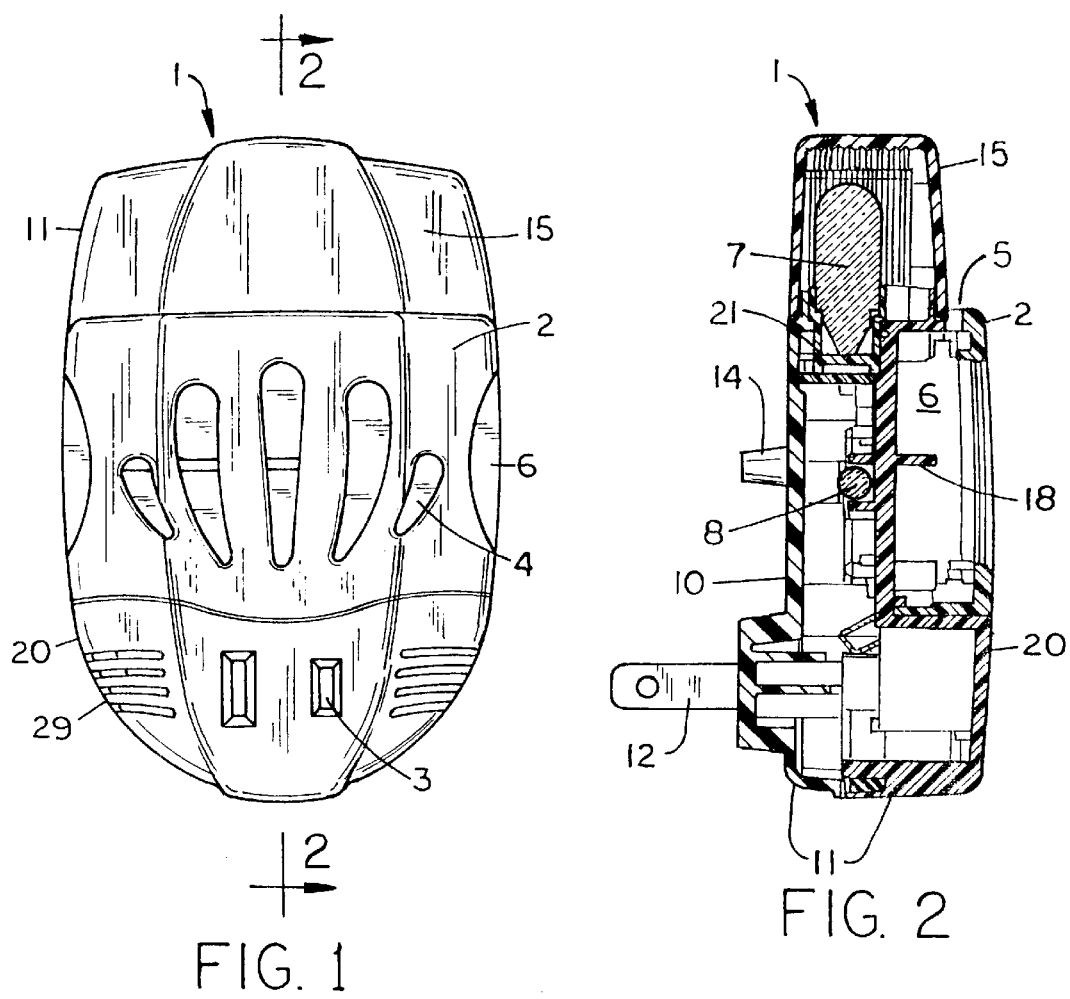
FIG. 1 is a front external elevation of a thermal diffuser of the present invention.
FIG. 2 is a cutaway illustration of said diffuser, taken on line A—A of FIG. 1.

FIG. 1 illustrates a frontal view of a thermal diffuser, 1, showing decorative features as well as functional aspects of the invention. The housing or external surface, 11, of the dispenser or thermal diffuser, 1, may be of any acceptable material, such as a moldable plastic material or a hard synthetic rubber composition. Due to low cost, and ease of manufacture, preferred materials include polypropylene, nylon, and the like. The housing, 11, constitutes the outer shell of the diffuser, and is comprised of a number of subassembly pieces which clip or fit snugly together during assembly, preferably permanently, so as to prevent the consumer from accidentally damaging, or gaining access to the electrical circuitry contained within. Such subassemblies may be glued or cemented together by known adhesives, or may be of such close tolerance fit to prevent easy disassembly. In the preferred embodiment, the housing assemblies are ultrasonically welded together, and the lamp cover or lens is a snap fit. These subassemblies, which are illustrated in greater detail in FIGS. 2–7, include the front cover, 2, the night light cover or lens, 15, the plug deck assembly, 10 (not shown in FIG. 1), and the main housing assembly, 20. It will be observed that the exterior of the thermal diffuser is comprised of exterior portions of the front cover, the main housing assembly, and the plug deck, as well as the night light lens.

In FIG. 1, the night light lens, 15, is shown as the topmost element of the thermal diffuser. For low cost, and for ease of assembly, the night light lens is preferably a molded plastic, such as clear polypropylene, polycarbonate, styrene, or, preferably, nylon, so shaped as to fit tightly over the top portions of the main housing assembly, 20, and plug deck assembly, 10, as shown in FIG. 7, when joined, and having clip receptacles therein to receive corresponding clip means, not shown, on said assemblies. Other means for joining said assemblies will, of course, be apparent to those skilled in the art. While the night light lens may preferably be of a transparent plastic molding, it may also be translucent, colored, and/or decoratively adorned. The lens may also take any desired shape, and may be in a decorative form if so desired. Further, while the Figures illustrate the invention with the night light at the top, it is possible to orient the dispenser with the night light at the bottom or to the side, dependent upon the electrical outlet utilized.

FIG. 1 further illustrates the exterior frontal view of the front cover, 2, having air diffusion outlets, 5, therein for diffusion of vaporized active material to the atmosphere. Such outlets, constituting a slot at the top of the front cover, provide for a chimney effect so that air movement occurs across the front of the active material cartridge, may be formed in the front face assembly during molding thereof, and also provide a path for the diffusion of active material to the atmosphere. Air diffusion inlets, 4, are illustrated in the front of the cover, providing a source of air flow through the diffuser. Such inlets are preferably decorative in nature as well, and formed in the front face assembly during molding thereof.

In addition, the opening to a slot, 6, is provided in the side of the front cover to receive, for example, a specially adapted active material cartridge or container (not shown). Within this slot are rails, 18, which engage protrusions or indents on the cartridge during insertion, and hold the cartridge in position within the slot. With the cartridge inserted into the slot, 6, the diffuser is plugged into an electrical outlet via the electrical plug, 12. Once plugged in, the heating unit heats the active material cartridge, releasing, for example, fragrance into the atmosphere. Once the fragrance cartridge is spent, it may be removed and replaced. It should be noted that the present invention is not limited to use with these specially designed refill cartridges. The diffuser of the present invention may also be designed as a container which itself holds a suitable active material, such as a fragrance or insect repellent, to be heated and emitted. Alternatively, a port could be provided to which separately provided containers might be attached. Preferred containers for the present invention comprise tray shaped cartridge containers having a plastic laminate over the active material, said laminate comprising an outer removable layer which is impermeable to the both liquid and vapor forms of said active material, and an inner layer which is impermeable to the liquid form, but permeable to the vapor form of said active material. Upon removal of the outer layer, said active material may diffuse through the remaining layer to be released to the atmosphere. Typical of said containers are those refill units sold under the tradename GLADE®, by S. C. Johnson and Sons, Racine, Wis. Such cartridges are illustrated in U.S. Pat. No. 4,849,606, incorporated herein by reference.

Also shown in FIG. 1, at the lower part of the diffuser, in the external forward face of the main housing assembly, 20, is an electrical receptacle, 3, into which an external plug may be inserted. The electrical elements behind this receptacle are shown more clearly in FIGS. 2–5. In addition, if it is desired to provide the night light element of this invention with an ambient light sensor for automatic operation, the sensor may preferably be located behind a sensor grill, 29, in a position where it will not be significantly illuminated by the night light bulb, as well as being protected from accidental breakage. The night light of the present dispenser may, of course, be controlled by a conventional on/off switch, but it is preferably controlled by automatic circuitry including a light sensor device. While FIG. 1 illustrates two sensor grills, for symmetry, it is preferable that for ease and economy of production, only one set of grills would be cut completely through the housing, and the other would be merely decorative. While the Figure illustrates the sensor grill as being on the left, it may be on either side of the housing, with a similarly configured decorative pattern on the opposite side.

FIG. 2 constitutes a side elevation of the thermal diffuser, 1, of FIG. 1, taken on line A—A. Shown herein are the night light lens, 15, the front cover assembly, 2, the main housing assembly, 20, and the plug deck assembly, 10, the external surfaces of which assemblies constitute the housing, 11. Also shown are the lamp, or night light bulb, 7, mounted on the night light circuitry board, 21, under the night light lens. Also shown, in side profile, is the opening, or slot, 6, which receives the active material container, and positioning rail 18. Inside the diffuser, heating element 8 is shown, while outside the housing are shown positioning wall spacers 14, which serve to stabilize the diffuser when it is plugged into a wall outlet by means of plug 12.

Figure 3:
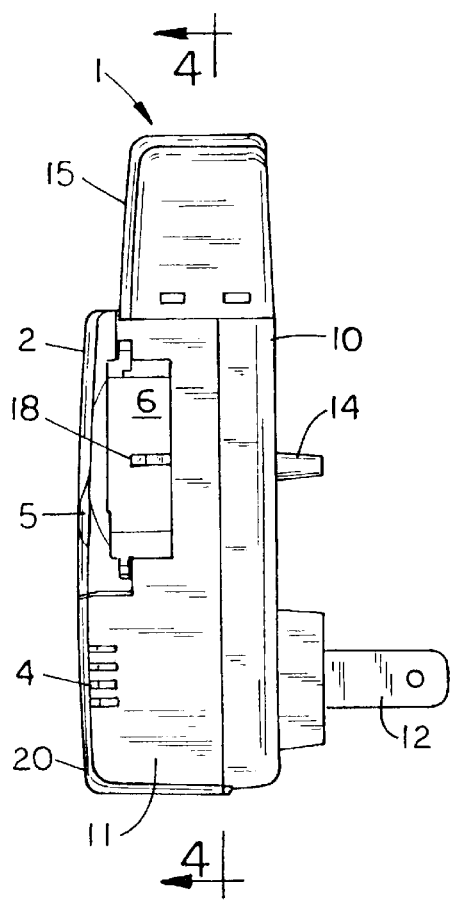
FIG. 3 is a side external elevation of a thermal diffuser of the present invention.

In FIG. 3, a side elevation of the thermal diffuser, 1, the exterior surface or housing 11, and night light lens, 15, are shown. Also shown are the thermal diffuser plug, 12, and the wall spacer 14, extending rearward of the plug deck assembly, 10. The opening, 6, for receipt of the active material cartridge, is shown from the open or receiving end, as is the positioning rail 18 in said opening.

Figure 4:
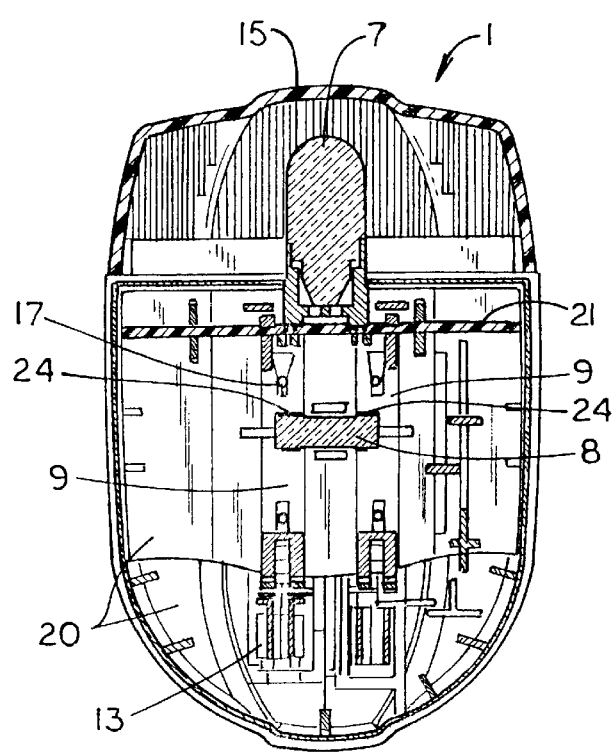
FIG. 4 is a cutaway illustration of said diffuser, taken on line B—B of FIG. 2.

FIG. 4, a cross sectional view of the diffuser of FIG. 3, taken on line B—B, provides a view of the interior of the diffuser, 1, looking from the rear toward the front thereof. Shown is the interior surface of the light lens 15, and the back of main housing assembly 20. Mounted to the back of the main housing assembly are heat transfer plates 9, in heat transfer contact with heating element 8, held in place by clip 24. Said heat transfer plates make electrical contact with the terminals of the male plug, 12 ( not shown), and being made of an electrically conductive material, such as copper, transfer power to the heating element 8, a coil resistance heater or metal oxide resistance heater, for example. Other small heating units may be used, such as PTC (Positive Temperature Coefficient) heaters, printed ink circuitry, or etched foil. Since the wall of the main housing assembly forms the back wall of the slot which receives the active material cartridge, the transfer plates thus act to transfer heat to the active material, thereby increasing the rate of diffusion thereof. Also in electrical contact with the heat transfer plates is the night light circuitry board, made of a suitable circuit board material, which provides mounting means and circuitry to provide electricity to the night light, and the optional illumination sensor and its circuitry. Also shown in FIG. 4 are retention clips 17, for positioning and retention of the heat transfer plates. The internal electrical structure (female assembly) of the receptacle 3 is also shown, at 13.

In FIG. 5, a plug deck assembly is illustrated, with the plug unit, 12, of the thermal diffuser shown in a "withdrawn" position, prior to being inserted into the plug deck assembly, 10, through the plug terminal positioning element 19. At the internal end of each of the prongs of the plug is a female assembly or receptacle for acceptance of an external plug through the external receptacle, 3. In this manner, the thermal diffuser of the present invention provides a plug-through outlet for the consumer. Also shown in FIG. 5 are various positioning and retaining protrusions, clips, or ribs, 17, which act to engage with the heater elements of the diffuser, which elements are generally mounted on the internal surface of the main housing assembly, 20, but are supported and aligned by said various ribs. Said ribs may be molded directly into the structure of the plug deck assembly, by procedures well known in the art. As is indicated in FIGS. 1 and 2, the outside surface of the edge portion of said plug deck assembly forms a portion of the outer surface or housing, 11, of said diffuser.

FIG. 6 illustrates the interior face of the main housing assembly, and the electrical elements which are attached thereto. Indicated on the exterior surface of said main housing assembly, 20, are the slot, 6, to receive the active material cartridge, and a positioning rail, 18, in said slot. In conjunction with the front cover assembly, 2, not shown in this figure, the main housing assembly forms the slot into which the active material cartridge may be placed. This cartridge, when in position, will be in close proximity to the forward face of the front surface of the main housing assembly, and heat generated at the back face of said surface will be transferred to the forward face, where it will act to evaporate active material in said cartridge. By means of retention clips 17, heat transfer plates, 9, are attached to the back face of said surface of said main housing assembly. These heat transfer plates, preferably of a material such as copper, brass, or bronze, which are both electrically and heat conductive, serve to both transfer heat from the heating element, 8, and electricity thereto. These heat transfer plates have spring contacts 26, by which electrical contact is made with the internal portions of the prongs of plug 12, not illustrated in this view, when said plug is inserted into an electrical outlet. Electricity is transmitted from the outlet, via plug 12, to spring contacts 26, of heat transfer plates 9. The heat transfer plates, 9, being electrically conductive, also act as an electrical bus, conducting electricity to the heating element clips, 24, and thus activate the heating element. The heating element may be chosen from such elements as PTC heaters, wire-wound resistors, encapsulated wire-wound resistors, etched foil, or metal oxide resistors, which are preferred for low cost, reliability, and convenience of packaging for manufacture. The resistance heater immediately commences radiation of heat, which is transferred to the inner surface of the wall of the main housing element, and by conduction to the heat transfer plates. The heat transfer plates, being in direct contact with said inner surface, thus greatly increase the efficiency of the heat transfer to the active material cartridge, which is in close proximity to the opposite side of the wall of said main housing element. Simultaneously, the heat transfer plates conduct electricity to the night light circuitry board, 21, via spring contact elements 27, at the end of said plates. Said contact elements are configured so as to contact electrically conductive circuits on the surface of said night light circuitry board, thus providing power to both the lamp, 7, and the illumination sensor, 22, which are electrically connected to said circuitry board. Also illustrated are lamp support 23, positioned to both support said night light bulb, 7, on said night light circuitry board, 21, and to cooperatively engage a correspondingly shaped opening, 25, in the surface of said main housing assembly, so as to aid in positioning of the night light bulb.

FIG. 7 illustrates the relative positioning of all elements of the present invention, viewed from the rear (wall side) of the plug-in diffuser. Shown are the plug deck assembly, 10, the main housing assembly, 20, the front cover assembly, 2, and the night light lens, 15. Shown as part of the plug deck assembly are the power plug, 12, and wall spacers 14, as well as retention clips 17 for engagement with correspondingly located clip receptacles, 16, in night light lens, 15. Similar retention clips 17 are present at the top surface of main housing assembly 20, for corresponding engagement with receptacles in the night light lens.

The electrical elements of the invention are illustrated in conjunction with the main housing assembly, of which they are preferably a portion. Heating element 8 is held in place by heating element clips, 24, which are in electrical and heat conductive contact with heat transfer plates 9, which also act as electrical bus bars to conduct power to the elements of the invention. Power is introduced to the plug-in diffuser via the terminals or prongs of plug 12, which prongs extend into the main housing assembly and contact the protrusions 26, of the heat transfer plates and via the heat transfer plates to contact elements 27, by which the flow of electricity is conducted to the night light circuitry board 21. The circuitry board comprises the necessary electrical contacts and circuitry, not shown, to power the night light bulb, 7, as well as the illumination sensor, not shown. The lamp is maintained in its position in the main housing assembly by means of lamp support 23, fitting into the correspondingly configured opening, 25, in the assembly. Also illustrated in FIG. 7, is the outer surface of the plug deck assembly and of the main housing assembly, which form the housing, 11, or external surface of the dispenser unit.

Also forming part of the external surface of the dispenser is the front cover assembly, 1, which has openings 5, for air diffusion or circulation of the heated active material, and positioning rail 18 to position the active material cartridge, not shown, in the slot. In the forward face of the main housing assembly are located corresponding positioning rails, and air diffusion inlets, 4, behind which the illumination sensor, not shown in this view, may be located, as well as the edges of the slot 6 into which the active material cartridge is placed.

As may be readily observed from the Figures, the operation of the thermal diffuser of the present invention is relatively straightforward. An air freshener prepared in accordance with this invention was made and tested, with the following observations. After insertion of an active material cartridge into slot 6, the diffuser unit was plugged into an electrical receptacle of a wall outlet, using diffuser plug 12. The heater unit, 8, was powered via electricity passing through the plug, the protrusions 26 of the heat transfer plates, the heat transfer plates 9, and the heating element clips 24. Thus activated, the heater generated heat, which was transferred by radiation and by conduction through heat transfer plates 9, to the back surface of the wall of the main housing assembly, 20. The active material cartridge, being in close proximity to the opposite side of said wall of said main housing assembly, absorbed heat energy, causing active material to be heated and evaporated, said active material diffusing into the air and passing into the atmosphere through diffusion outlets 5. The active material was an air freshener composition comprising Glade® Mountain Berry fragrance, available from S. C. Johnson & Son, Inc., of Racine, Wis. The air freshener dispenser was stabilized in the wall outlet by the presence of the wall spacers, 14, on the rear of the unit, and generated a pleasant and effective air freshener scent. In addition, the lamp of the unit automatically lit when the ambient light in the room was decreased to a level approximating that of night time. That is, when the ambient light was prevented from reaching the sensor, 22, by blocking the sensor grill, 29, the lamp 7 was illuminated. In addition, a table lamp was plugged into the receptacle, 3, on the front of the air freshener dispenser. At night, when the night light bulb was illuminated, with the sensor grill uncovered, the table lamp was turned on, causing the night light to go out. After a period of about 45 days, the air freshener cartridge was expended. The depleted cartridge was removed, by sliding it out of the slot, 6, and replaced with a new cartridge containing a different active material. After a brief period, the new active material was detected in the atmosphere surrounding the diffuser unit.

As previously indicated, the active material may be selected from a large variety of materials suitable for diffusion into the atmosphere, such as an active ingredient selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof. The most commonly employed active materials are fragrances and air fresheners. Preferably, the fragrance or air freshener comprises one or more volatile organic compounds which are available from perfumery suppliers such as Firmenich Inc., Takasago Inc., Noville Inc., Quest Co., International Flavors & Fragrances, and Givaudan-Roure Corp. Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components. Synthetic types of fragrance compositions either alone or in combination with natural oils are described in U.S. Pat. Nos. 4,324,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

A liquid fragrance may also be formed into a thixotropic gel by the addition of a thickening agent, such as a cellulosic material, a polymeric thickener, or a fumed silica of the type marketed under the Cabosil trademark by Cabot Corporation. A fragrance ingredient can also be in the form of a crystalline solid, which has the ability to sublime into the vapor phase at ambient or slightly elevated temperatures. A crystalline fragrance starting material can be selected from organic compounds which include vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evemyl, and the like. This type of fragrance can contribute a long term air-treatment capability to an air freshener dispenser device for use in the present invention. However, it is noted that the present invention is not dependent upon the specific active material to be dispensed, but upon the novel configuration and capability of the thermal diffuser disclosed.

INDUSTRIAL APPLICABILITY

While the present invention has been described with respect to what is at present considered to be the preferred embodiments, it is to be understood that the invention is not to be limited to the disclosed embodiments. To the contrary, the invention is intended to cover various modifications and equivalent arrangements within the spirit and scope of the appended claims. The scope of the following claims is to be accorded the broadest interpretation so as to encompass all such modifications and equivalent formulations and functions. The diffuser of the present invention may be manufactured of commonly available materials, and may utilize readily available replacement cartridges in the operation thereof. The electrical circuitry and electrical elements employed are commonly available and known to one skilled in the art, although not in the configuration and arrangement of the present invention.

What is claimed is:

1. A plug-in diffuser, for use with a substance to be thermally diffused, said diffuser comprising:

a. an outer housing;

b. a male electrical plug extending outwardly from the rear of said housing;

c. a female electrical receptacle on the front of said housing having direct electrical contact with said male electrical plug, thereby providing plug-through capability;

d. an opening in said outer housing for receipt of an active material container, said opening being located between the front cover of said housing and an inner wall within said housing;

e. an electrical resistance heater electrically connected between the terminals of said male electrical plug by means of parallel electrically conductive metal plates;

wherein said parallel electrically conductive plates extend from said male electrical plug terminals to a night light circuitry board electrically connected between said parallel metal plates within said housing, and said electrically conductive metal plates also comprise heat transfer plates in heat conductive contact with said inner wall within said housing, whereby said electrically conductive metal plates both conduct electricity to said night light circuitry board, and transfer heat to said active material via said inner wall; and f. an electric lamp electrically connected to said night light circuitry board, and having a night light lens over said electric lamp and affixed to said housing.

2. The plug-in diffuser of claim 1, wherein said housing is a molded plastic material having air diffusion openings therein.

3. The plug-in diffuser of claim 1, where in said night light lens is a transparent plastic.

4. The plug-in diffuser of claim 1, wherein said active material container comprises a replaceable plastic tray having a vapor permeable cover thereupon.

5. The plug-in diffuser of claim 4, wherein said active material is selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof.

6. The plug-in diffuser of claim 5, wherein said active material is selected from the group consisting of air fresheners and fragrances.

7. The plug-in diffuser of claim 1, wherein the circuitry for said night light comprises an on/off switch.

8. The plug-in diffuser of claim 1, wherein the circuitry for said night light comprises an automatic on/off circuit and ambient light sensor.

9. The plug-in diffuser of claim 1, wherein the circuitry for said night light comprises a non-replaceable lamp.

10. A heated dispenser of active materials, said dispenser comprising a container of active material, an electric resistance heater, and plug-through electrical circuitry, wherein:

a. said dispenser comprises a male electrical plug extending rearwardly from said dispenser with a female electrical receptacle on the front of said dispenser in direct electrical contact with said male electrical plug;

b. said dispenser further comprises electrically conductive elements extending from the terminals of said male plug to the electric resistance heater; whereby c. said electrically conductive elements conduct electricity to a night light circuitry board to thereby power a night light connected to said circuitry board in said heated dispenser, and said electrically conductive elements further conduct heat from said resistance heater to said container of active materials to cause said active materials to evaporate from said container.

11. A heated dispenser as set forth in claim 10, wherein said container of active materials comprises a plastic tray having a vapor permeable cover over an active material selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof.

12. A heated dispenser as set forth in claim 11, wherein said active material is selected from the group consisting of fragrances and air fresheners.

13. A heated dispenser as set forth in claim 10, wherein said heater comprises a metal oxide resistance.

14. A heated dispenser as set forth in claim 10, wherein said night light circuitry board further comprises an automatic control for said night light.

* * * * *